| United States Patent [19] | [11] 4,112,596 |
|---|---|
| Fletcher et al. | [45] Sep. 12, 1978 |

[54] PSEUDO PALATE USEFUL FOR DIAGNOSIS AND TREATMENT OF SPEECH IMPAIRMENT

[76] Inventors: Samuel G. Fletcher, 2208 Avanti La., Birmingham, Ala. 35226; Martin J. McCutcheon, 2313 Garland Dr., Birmingham, Ala. 35216

[21] Appl. No.: 756,070

[22] Filed: Jan. 3, 1977

[51] Int. Cl.² ............................................. G09B 19/04
[52] U.S. Cl. ...................................... 35/35 R; 3/1.1;
128/2 S; 35/17
[58] Field of Search ...................... 35/35 R, 17; 32/19,
32/40 R; 128/2 S; 3/1, 1.1

[56] References Cited

U.S. PATENT DOCUMENTS

| 3,239,935 | 3/1966 | Shackelford | 32/19 |
| 3,417,743 | 12/1968 | Carrera | 128/2 S |
| 3,983,865 | 10/1976 | Shepard | 128/2 S |

*Primary Examiner*—William H. Grieb
*Attorney, Agent, or Firm*—Hugh P. Carter

[57] ABSTRACT

A pseudo palate is formed of a thin sheet of material shaped to the contour of the palate of a person whose speech is to be tested. On the lingual surface of the sheet is an array of electrodes located in the lingual contact areas of the palate and spaced apart predetermined distances. Conductors attached to the electrodes are embedded in the sheet and are grouped together in at least one bundle to exit from the palate at its posterior, into the buccal cavity of the patient's mouth where the bundle of conductors may exit from the mouth at a corner thereof. These conductors are attached to suitable instrumentation which may give a visual or possibly aural signal corresponding to the position of the tongue when the patient makes, or attempts to make, designated speech sounds. The electrical portion of the system may comprise means to impose a small voltage on the body of the patient, whereby when the tongue touches the electrodes, circuits are completed, thus providing a display corresponding to the position of the tongue.

5 Claims, 5 Drawing Figures

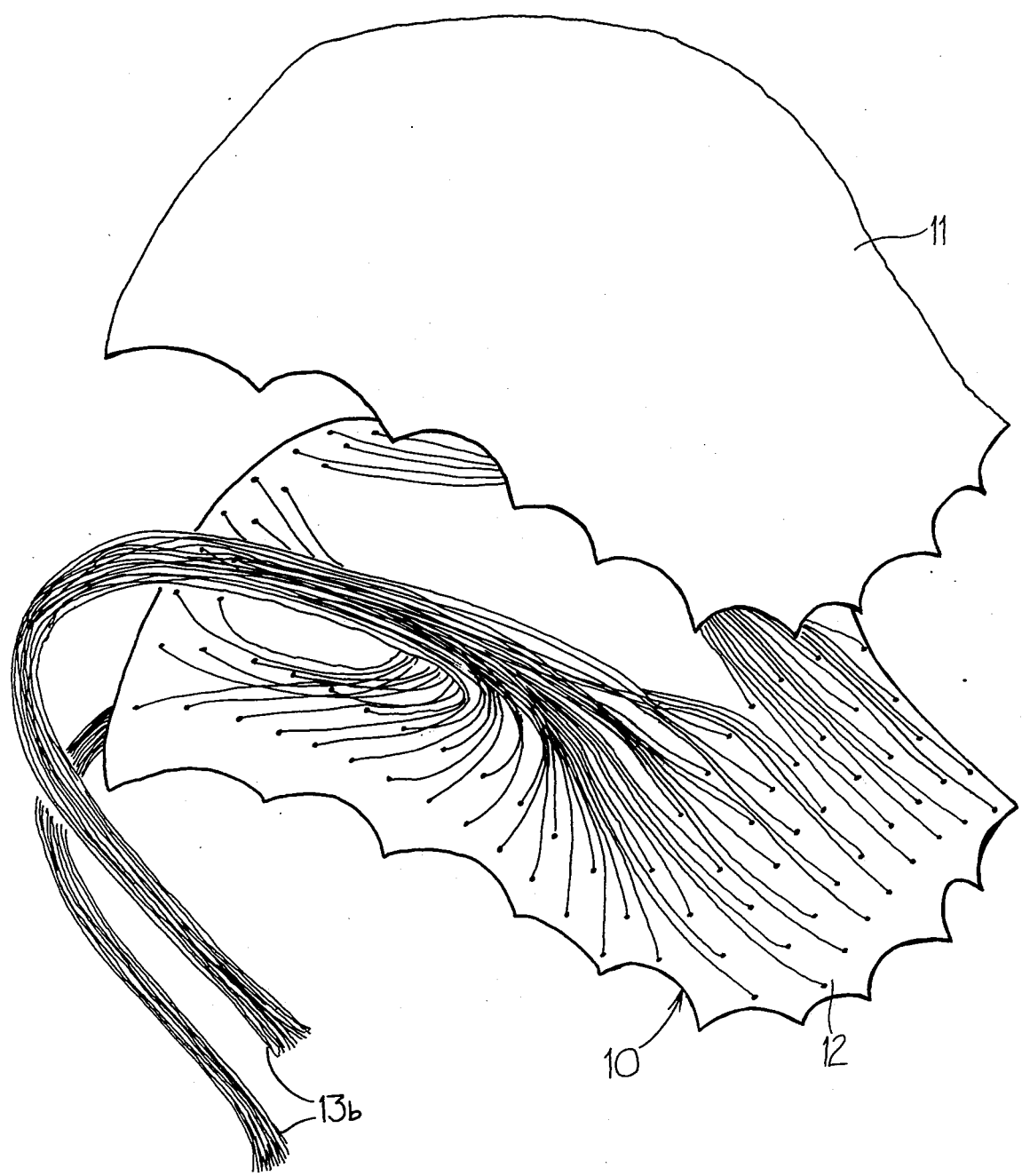

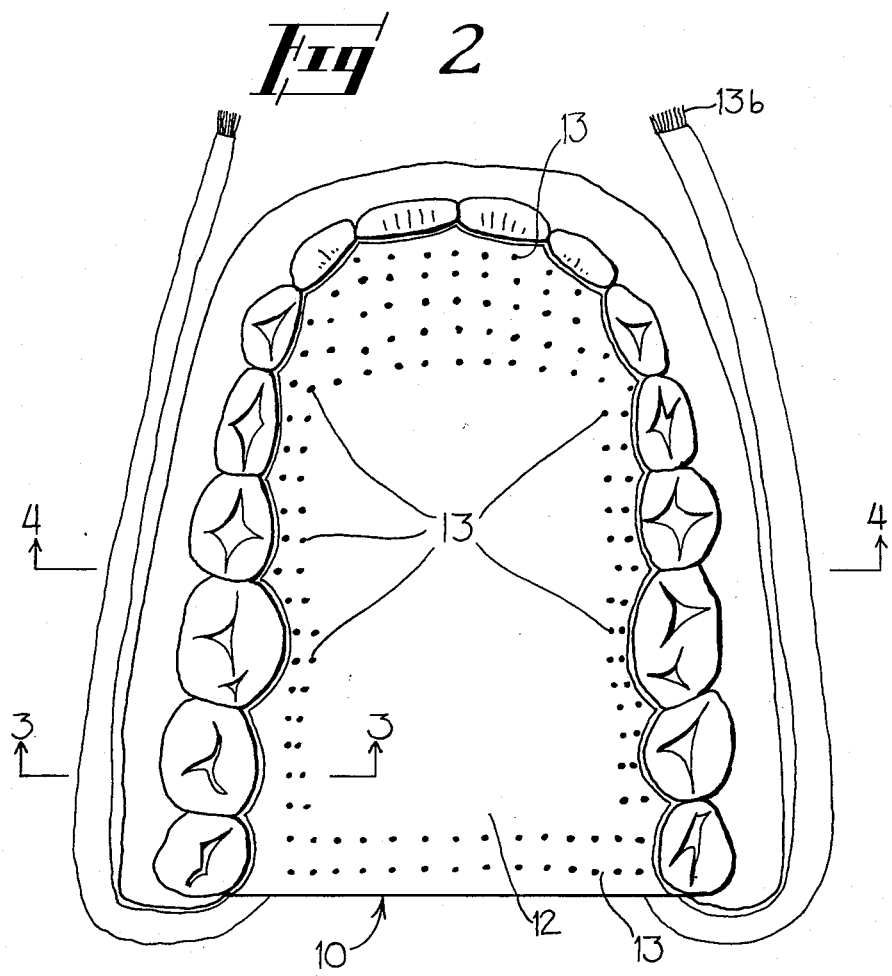
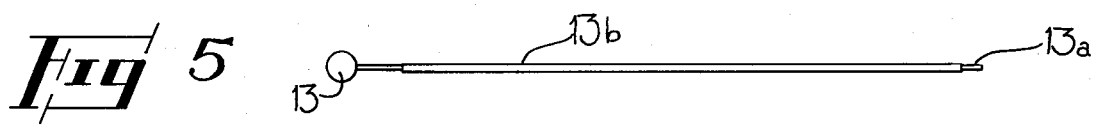
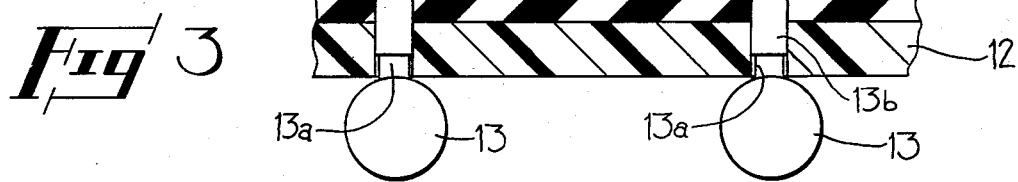
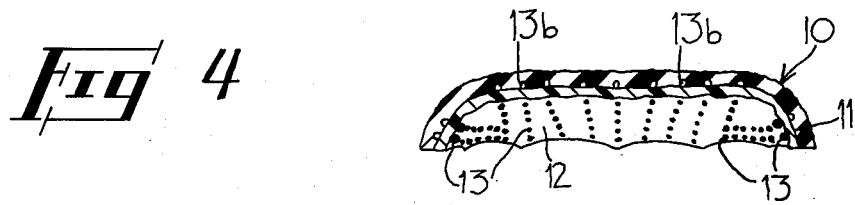

PSEUDO PALATE USEFUL FOR DIAGNOSIS AND TREATMENT OF SPEECH IMPAIRMENT

This invention relates to apparatus particularly useful in the diagnosis and treatment of speech impairment.

Heretofore in this art attempts have been made to provide pseudo palates for use in describing speech production. However, in the diagnosis and treatment of speech impairment, insofar as we are aware such attempts have not been marked with any great degree of success. Primarily, the previous pseudo palates have been too bulky, non-uniform in thickness and difficult and expensive to construct. Further, prior pseudo palates have failed to incorporate what we now have discovered to be an advantageous spacing and number of electrodes. Suffice it to say that so far as we are aware prior attempts in this particular field have left much to be desired.

In view of the foregoing an object of our invention is to provide a pseudo palate which may be placed in the mouth of a patient and which is so constructed as to interfere in minimum fashion with the natural shape and function of the oral cavity, insofar as making speech sounds is concerned.

Another object of our invention is to provide a pseudo palate formed of a sheet, preferably a composite sheet, of thin, electrically non-conductive material, moldable to fit the shape of the individual palate of the person to be treated, together with a plurality of electrodes located on the lingual surface of the palate and conductors for each of the electrodes which may be led from the mouth to suitable apparatus used in presenting a pattern signal corresponding to the lingual contact with the inserted pseudo palate.

A further and more specific object of our invention is to privide a pseudo palate in which the array of electrodes on the lingual surface thereof is laid out in a definite, predetermined pattern, tailored to each individual patient, depending upon the individual impairment to be determined and treated.

Yet another and more specific object is to provide a pseudo palate of sheet-like material on the order of 0.1 to 0.5 mm in overall thickness, the aforementioned electrodes being properly arrayed on the lingual contact surfaces thereof, together with conductors for each of the electrodes which exit from the mouth and may be attached to suitable signal processing and displaying equipment.

A pseudo palate illustrating features of our invention is shown in the accompanying drawings, forming a part of this application, in which:

FIG. 1 is a wholly diagrammatic, exploded view of a pseudo palate incorporating features of our invention;

FIG. 2 is an enlarged, diagrammatic view looking upwardly into the mouth of a patient with our improved pseudo palate in place;

FIG. 3 is a greatly enlarged sectional view taken generally along line 3—3 of FIG. 2 and designed to illustrate the general relative thicknesses of the layers of material making up our improved pseudo palate;

FIG. 4 is a detailed sectional view taken generally along line 4—4 of FIG. 2, the thicknesses of the layers of material forming the pseudo palage being exaggerated and the view being rotated 180° from the position of FIG. 2; and, FIG. 5 is an enlarged fragmental detail view of one of the electrodes and attached conductor.

Referring now to the drawings for a better understanding of our invention, we show in FIG. 1 our improved pseudo palate indicated generally by the numeral 10. As will be understood, FIG. 1 is an exploded view in which the palatal layer 11 has been vertically separated from the lower or lingual layer 12 of the composite sheet making up our improved palate.

More in detail, we preferably employ for the lingual layer 12 a sheet of so-called "plastic" material, by way of example, a sheet of material having generally the physical and chemical characteristics of polyvinyl chloride on the order of 0.1 mm in thickness.

To form our improved pseudo palate to fit the contour of the palate of an individual to be diagnosed or treated we first make from a moldable material an impression of the patient's palate, including the upper teeth. When this material has set we caste an impression of the same from orthodonic stone material thus to obtain an exact replica of the palate itself and those portions of the teeth which enter, or should enter, into the speech process. Next we lay out a grid of lines on the lingual surface of the impression as will now be described.

The first step in laying out the grid lines is to select two points on the stone model corresponding to the posterior margin of the alveolar ridges. A third point is located at the posterior margin of the incisal foramen. Employing suitable instruments such as a scriber mounted on a vernier height guage, and using the points above mentioned, we lay upon the surface of the stone model a grid work of the lines which we stated are preferably 1 mm apart.

We now place the stone model, which material is pervious to air, over a vacuum chamber. A sheet of the material to form the layer 12 is heated and vacuum formed on the stone model to the exact contour of the subject's mouth. The material is then trimmed to eliminate interference with occulusion.

The next step is to select a location for the array of electrodes which is to be placed on the lingual surface of sheet 12. With the now formed, clear transparent sheet 12 again positioned in the stone model, the grid lines are clearly visible through the sheet 12. Having in mind the type of examination and treatment to be carried out on the individual patient the location, spacing and numbering of the array of individual electrodes 13 on the lingual surface of the pseudo palate is now determined. Thus, and by way of example as illustrated in FIG. 2, for a general investigation of the speech pattern of the patient the array shown in that figure would be used. Thus, and specifically there are about 96 electrodes 13 at the anterior and posterior portions of the pseudo palate and along each side. However, if it were desired to investigate only the ability properly to articulate the "S" sounds, we have discovered that the electrodes must be concentrated on the anterior areas of the palate with a spacing of 1 to 2 mm. However, in no instance need these electrodes be closer together than 1 mm, that is, no closer together than the spacing of the 1 mm grid lines.

In the example given in FIG. 2 we illustrate the condition in which the electrodes 13 are spaced apart about 3 mm. In certain instances we have found that spacing of up to 5 mm is useful. By way of example, the wider spacing may be used when investigating combinations of sounds such as in "six", "box", "cash", etc.

Having now decided where the electrodes are to be located for the particular type of investigation desired, small holes are punched through the sheet 12 at the locations selected. The electrodes 13 preferably are formed on the ends of the conductors 13a by a melting process in which the ends of the wire, preferably copper, simply are melted. The capillary action of the molten metal forms (on wire of the size hereafter indicated) generally spherical balls approximately 0.2 mm in diameter. It will also be noted that the conductor 13a is covered with an insulating material 13b.

After the electrodes 13 are formed on the ends of the required numbers of wires and before they are placed on the palate, the electrodes 13 are plated with a suitable corrosive resistant or non-reacting material such as gold.

Having now selected the proper locations for the electrodes the individual conductors 13a which, by way of example, may be 38 gauge (American wire gauge) copper wire insulated with a thin layer of non-conducting plastic material, are threaded through the holes in layer 12 until the electrodes carried by each conductor lie on the lingual surface of the pseudo palate. A suitable wire may be obtained from the Belden Company, Chicago, Illinois, and is known as their No. 8045 magnet wire.

With the wires threaded through the selected openings in the sheet 12 they are now bundled, preferably into two groups, as illustrated in FIG. 1 and are led to the posterior-lateral corners of the palate where they can exit into the buccal cavity of the patient's mouth and thence may be led forwardly to exit from the corners of the mouth. With the conductors thus laid in place we now coat the palatal surface of the stone model with a release agent such as petroleum jelly and then with a thin layer of elastomeric material. This material may simply be brushed onto the surface of the stone model. The now formed sheet 12, with the wires lying closely adjacent its upper surface, is now inserted into the elastomeric coated cavity of the stone model. The material forming layer 11 then self-cures and adhers to the upper surface of layer 12. This process completely bonds the two together, forming a unitary structure which preferably is no more than 0.3 mm in thickness. The elastomeric material is softer or less stiff than the sheet 12 so as to fit snugly and comfortably in the patient's mouth and still thin enough not to disturb speech production.

After carrying out the foregoing we now have in hand a pseudo palate which accurately fits the patient's mouth, which carries an array of electrodes specifically designed, located, spaced and shaped to be contacted by the tongue, or which should be contacted by the tongue, if the patient speaks properly.

With the pseudo palate in place a small voltage on the order of 250 millivolts and on the order of 10 KHz is impressed upon the patient's body as for instance by securing an electrode to his wrist. The conductors lead to a suitable form of processing and display equipment. As the patient utters or attempts to utter specifically designated sounds, or words, the pattern of his speech, dependent upon the contact of the tongue with the electrodes, is reflected in a suitable display which may be shown to the patient himself for corrective purposes or which may be interpreted by a clinician.

For a more complete dissertation on the method of using our improved pseudo palate attention is called to an article entitled "DYNAMIC PALATOMETRY" by the applicants and Dr. Matthew B. Wolf, published in "The Journal of Speech and Hearing Research", December 1975, Volume 18, No. 4. The publication release date of which Journal was Jan. 13, 1976. Suffice it here to say that our invention forming the subject of this application concerns itself with the pseudo palate per se. The use of the same not herein detailed may be ascertained by reference to said article.

In view of the foregoing it will be apparent that we have devised an improved pseudo palate useful in the art of speech diagnosis and therpy. Our invention is characterized, as stated, by the fact that when in place in the patient's mouth it interferes in minimum fashion with the normal functions of the palate and tongue during speech production. By making the pseudo palate extremely thin, in many instances it will be held in the mouth simply by surface tension of the mouth fluids. Even in those instances where such is not the case the use of a small amount of denture adhesive is all that is required, again, minimizing interference with speech.

While we have shown our invention in but one form, it will be obvious to those skilled in the art that it is not so limited but is susceptible of various changes and modifications without departing from the spirit thereof.

What we claim is:

1. A pseudo palate comprising:
   (a) a sheet of electrically non-conducting material of from about 0.1 to about 0.5 mm thick and shaped to conform to the palate of a person,
   (b) a plurality of electrodes on the lingual surface of the pseudo palate positioned in a predetermined pattern thereon, and
   (c) a conductor for each electrode embedded in the sheet and exiting adjacent the rear portion of the pseudo palate, whereby through the use of other apparatus the type and extent of lingual contact may be determined.

2. A pseudo palate as defined in claim 1 in which said sheet is formed of at least two layers, said conductors lying between the said layers.

3. A pseudo palate as defined in claim 2 in which the lingual layer of said sheet is formed of sheet material having a stiffness greater than the palatal layer thereof.

4. A pseudo palate as defined in claim 2 in which the lingual layer of said sheet is of a material possessing generally the physical characteristics of sheet polyvinyl chloride and having a thickness of about 0.1 mm, the palatal layer being of an elastomeric material on the order of 0.2 mm in thickness.

5. In a pseudo palate useful for diagnosis and treatment of speech impairment,
   (a) a sheet of electrically non-conductive material of from about 0.1 to about 0.5 mm thick and shaped to conform to the palate of a person,
   (b) an array of electrodes on the lingual surface of the sheet in the lingual contact areas thereof and spaced apart on the order of from 1 to 5 mm, and
   (c) conductors for the electrodes embedded in the sheet and brought together to form at least one bundle of conductors which exits from the rear portion of the pseudo palate into the buccal cavity of a patient's mouth thence exits at a corner of the mouth.

* * * * *